(12) United States Patent
Seeney et al.

(10) Patent No.: US 8,001,977 B2
(45) Date of Patent: Aug. 23, 2011

(54) DEVICE FOR MOVING MAGNETIC NANOPARTICLES THROUGH TISSUE

(75) Inventors: Charles E. Seeney, Edmond, OK (US); William A. Yuill, Edmond, OK (US)

(73) Assignee: NanoBioMagnetics, Inc., Oklahoma City, OK (US)

( * ) Notice: Subject to any disclaimer, the term of this patent is extended or adjusted under 35 U.S.C. 154(b) by 1235 days.

(21) Appl. No.: 11/400,620

(22) Filed: Apr. 6, 2006

(65) Prior Publication Data

US 2006/0228421 A1 Oct. 12, 2006

(51) Int. Cl.
*A61B 19/00* (2006.01)
(52) U.S. Cl. .................................................... 128/899
(58) Field of Classification Search ............. 600/9–15; 128/897–899; 606/130; 435/455–467
See application file for complete search history.

(56) References Cited

U.S. PATENT DOCUMENTS

| | | | |
|---|---|---|---|
| 5,753,477 A * | 5/1998 | Chan | 435/455 |
| 6,447,440 B1 * | 9/2002 | Markoll | 600/13 |
| 7,465,579 B2 * | 12/2008 | Hatakeyama et al. | 435/285.2 |
| 2002/0086842 A1 * | 7/2002 | Plank et al. | 514/44 |
| 2002/0147424 A1 * | 10/2002 | Ostrow et al. | 604/20 |
| 2005/0271732 A1 | 12/2005 | Seeney et al. | |
| 2007/0196281 A1 * | 8/2007 | Jin et al. | 424/9.34 |
| 2007/0231908 A1 * | 10/2007 | Cai et al. | 435/459 |

FOREIGN PATENT DOCUMENTS

WO WO 01/17611 A1 * 3/2001

OTHER PUBLICATIONS

Donald L. Miller, MD, Why Use Remote Guidance to Steer Catheters and Guide Wires?, Radiology, Aug. 2004, p. 313-14, vol. 232, No. 2.
Q A Pankhurst, et al, Applications of Magnetic Nanoparticles in Biomedicine, J.Phys. D: Appl. Phys., Jun. 2003, R176-R181.

* cited by examiner

*Primary Examiner* — Charles A Marmor, II
*Assistant Examiner* — Catherine E Burk
(74) *Attorney, Agent, or Firm* — Dunlap Codding, P.C.

(57) ABSTRACT

The movement of magnetically responsive nanoparticles through a membrane is significantly enhanced by using a varying magnetic field gradient. The magnetic field varies in intensity and/or direction and can be achieved by mechanically varying the position of a magnet with respect to the membrane, or by oscillating the strength of one or more electromagnets.

20 Claims, 3 Drawing Sheets

DEVICE FOR MOVING MAGNETIC NANOPARTICLES THROUGH TISSUE

This application claims priority of U.S. Provisional Patent Application Ser. No. 60/669,681 filed Apr. 8, 2005.

BACKGROUND OF THE INVENTION

1. Field of the Invention

The present invention relates generally to delivery of substances through membranes or tissue within a body, and more particularly, to a method and device for delivery of particles through membranes and tissue within a body.

2. Background of the Invention

Nanoparticles generally refer to particles having at least one dimension of about 100 nanometers or less. Magnetic nanoparticles offer many possible medical treatment possibilities due to their very small size and the ability to manipulate their movement using an externally applied magnetic field gradient. A major goal in medical applications using magnetic nanoparticle carriers is to increase deposition in a specific target area so as to increase the dose in the affected area and to allow less dosage in non-affected areas. For example, the particles may be used as carriers for pharmaceuticals, such as anticancer drugs, and the carrier particles may be magnetically targeted to a specific area of the body such as a tumor. Other applications may involve directing the particles toward and embedding the particles in a target organ tissue in order to impart magnetic properties to the target.

In many applications of this technology, what is needed is a method for improving the rate and extent of penetration of magnetic nanoparticles through a membrane or tissue. These and other objectives will be better understood with reference to the following disclosure.

SUMMARY OF THE INVENTION

The present invention is directed to moving magnetically responsive nanoparticles, and more specifically, to moving magnetically responsive nanoparticles through a membrane within a body. A device of the present invention generates a varying-gradient magnetic field for moving magnetically responsive nanoparticles through a membrane. The device comprises one or more magnets for producing a magnetic field at the membrane. At least one magnet is connected to a controller which operates to vary, in a repetitive manner, the magnetic field gradient produced at the membrane by the one or more magnets.

In one embodiment the device includes an electromagnet with a controller varying the power to the magnet in a repetitive manner. In another embodiment, the physical position of the magnet is repeatedly changed with time.

The present invention also includes a system for moving magnetically responsive nanoparticles through a membrane. The system comprises a means for introducing magnetically responsive nanoparticles into a body, and a magnetic field generator. The magnetic field generator is adapted to produce a repetitively-varying magnetic field gradient for moving the nanoparticles through the tissue.

The present invention additionally includes a method of moving magnetically responsive nanoparticles through a membrane within a body comprising the following steps. The magnetically responsive nanoparticles are introduced into the body. The nanoparticles are then moved through the membrane using a repetitively-varying magnetic filed gradient.

Other features and advantages of the present invention will be readily apparent to those skilled in the art upon a reading of the description of preferred embodiments which follows when taken in conjunction with the accompanying drawings.

DESCRIPTION OF THE PREFERRED EMBODIMENTS

In proposed medical treatment applications, magnetic nanoparticles are first caused to travel through the bloodstream. Once the particles have reached the target area, it is then desirable for the particles to penetrate the vessel wall and often to penetrate additional tissue. The rate and extent of penetration are important parameters for the success of these applications.

Conventional procedures to pull magnetically responsive particles through a fluid or tissue use fixed magnets to pull continuously in the same direction. Using a fixed magnet, the particles can be moved through a membrane, but the movement is relatively slow. The discovery outlined by this invention is that the rate of movement of superparamagnetic nanoparticles through a membrane is significantly faster using a magnetic field that oscillates or varies repetitively in direction and/or in strength, and particularly when using a field in which the direction of the magnetic field gradient varies repetitively with time. Thus, the method of the present invention comprises introducing magnetically responsive nanoparticles into the body, and moving the nanoparticles through a membrane using a repetitively-varying magnetic field directed at the membrane.

The phrase "repetitively-varying magnetic field" as used herein and in the appended claims is defined as "a magnetic field having repetitive changes or perturbations in the direction and/or strength of the magnetic field gradient." Varying the direction of the magnetic field gradient causes the force acting upon magnetic particles to vary in direction so as to aid particles in moving around individual molecules or fibers making up a vascular membrane and tissue. The particles can also be periodically relaxed by the magnetic field so as to disengage from the structure of the tissue and be free to move in the gradient when it is reestablished. These theories are believed to reflect actual mechanisms; however, the devices and methods of the invention do not depend on the accuracy of these theories.

Figure 1:
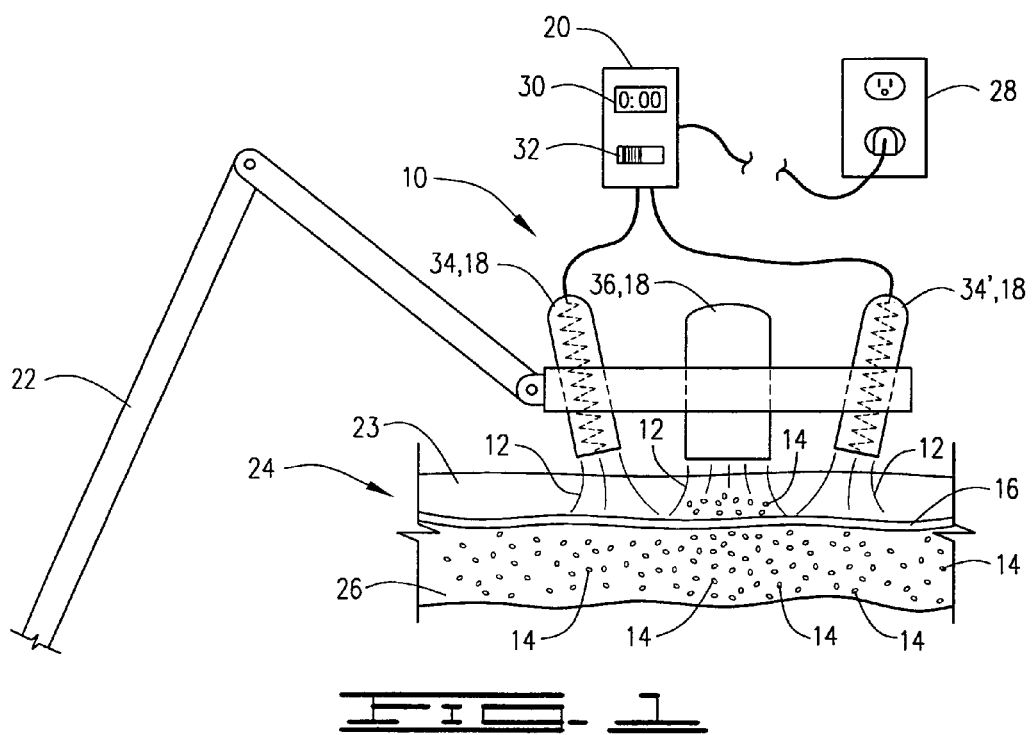
FIG. 1 is a diagrammatic illustration showing the use a device of the present invention.

Referring to FIG. 1, a magnetic field generating device 10 is shown for producing a varying-gradient magnetic field 12, illustrated by field lines, for moving magnetically responsive nanoparticles 14 through a membrane 16. One or more magnets 18 are needed for producing the magnetic field 12 at the membrane 16. A magnetic field gradient variation controller 20 is connected to at least one magnet and is operable to vary the magnetic field gradient of that magnet to cause a variation in the direction of the resultant gradient at the membrane 16. A positioning means 22 is connected to the magnets 18 and allows for positioning of the magnets 18 with respect to the membrane 16.

It is anticipated that movement of the particles can be optimized by modifying the composition and properties of the magnetic nanoparticles used. The magnetically responsive nanoparticles 14 preferably comprise ferromagnetic particles, more preferably superparamagnetic particles, and most preferably superparamagnetic particles comprising magnetite. The nanoparticles 14 may include a biocompatible shell and be used as carriers for bioactive substances such as pharmaceuticals or other materials such as gene or stem cells needed at a specific location in a body 24. For example, the particles could carry cancer treating drugs and be carried in a carrier fluid 26 such as the blood stream to a target tumor. In this case the particles must be moved from the bloodstream through membranes such as the wall of a blood vessel including the endothelium, as well as the membrane or tissue containing and surrounding the tumor cells. The term "nanoparticle" is used herein and in the appended claims to refer to all such particles, whether coated or carrying other chemicals, and regardless of whether the particles are present individually or in cemented clusters or agglomerates. The term "membrane" is used herein and in the appended claims in a broad sense to include arterial and vein walls as well as any tissue covering, lining, containing or separating target organs, tumors, cells, and the like in the body.

Other applications of the inventive technology include the embedding of superparamagnetic particles into the tissue of an organ in order to impart magnetic properties to that tissue and subsequently allow the organ to function with the aid of a magnet. Examples of this type application potentially include hearing devices and valves.

Suitable magnets include both permanent magnets and electromagnets. Commercially available permanent magnets include magnetic metallic elements, composites such as ceramics and ferrites, and rare earth magnets. Electromagnets are also readily available commercially.

In a preferred embodiment, the device comprises at least one electromagnet such that the magnetic strength can be oscillated or pulsed. (The term "oscillate" and all its forms are used broadly to include a pulse.) Design of electromagnets suitable for applications requiring oscillation and pulsing is well known to those skilled in the art.

The controller 20 may vary the physical position or movement of a magnet, or it may control the magnetic strength. For example, a controller may mechanically rotate one or more permanent or electromagnets. Preferably, controller 20 controls the power from a power source 28 to an electromagnet. More preferably, the controller comprises a timer 30 and a switch 32 for pulsing the power to the electromagnet by turning it off and on in a timed, repetitive fashion. Mechanical controller and electromagnet power controller design and manufacture are well known to those skilled in the art.

Figure 2A:
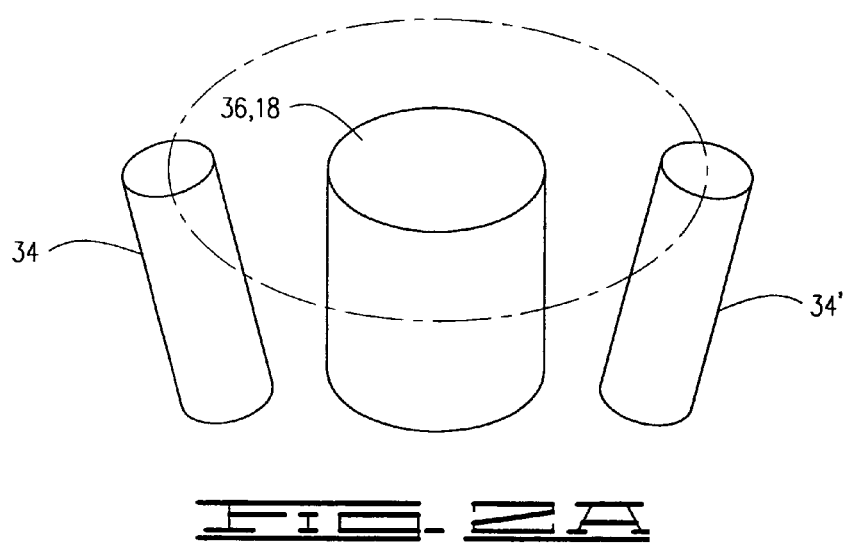
FIGS. 2A-2D are diagrammatic representations of magnet arrangements useful in the present invention.

Many different arrangements of magnets can be utilized to achieve a variable magnetic field gradient. A single electromagnet pulsed on and off can be used to provide a relaxation and reorientation time for the nanoparticles as described above. FIG. 1 and FIG. 2A show a preferred arrangement in which two electromagnets, 34 and 34', are alternately pulsed off and on while the strength of a main magnet 36 is constant. This arrangement provides variation in the direction of the magnetic field gradient. Main magnet 36 can be an electromagnet or a permanent magnet and is directed generally perpendicular to the membrane 16 while the electromagnets 34 and 34' are directed at an angle to this perpendicular.

Figure 2B:
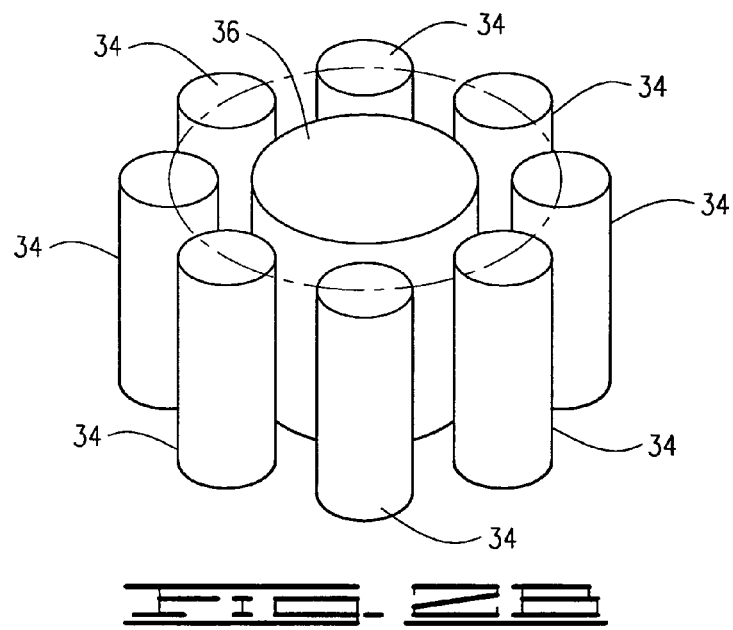
Figures 2C, 2D:
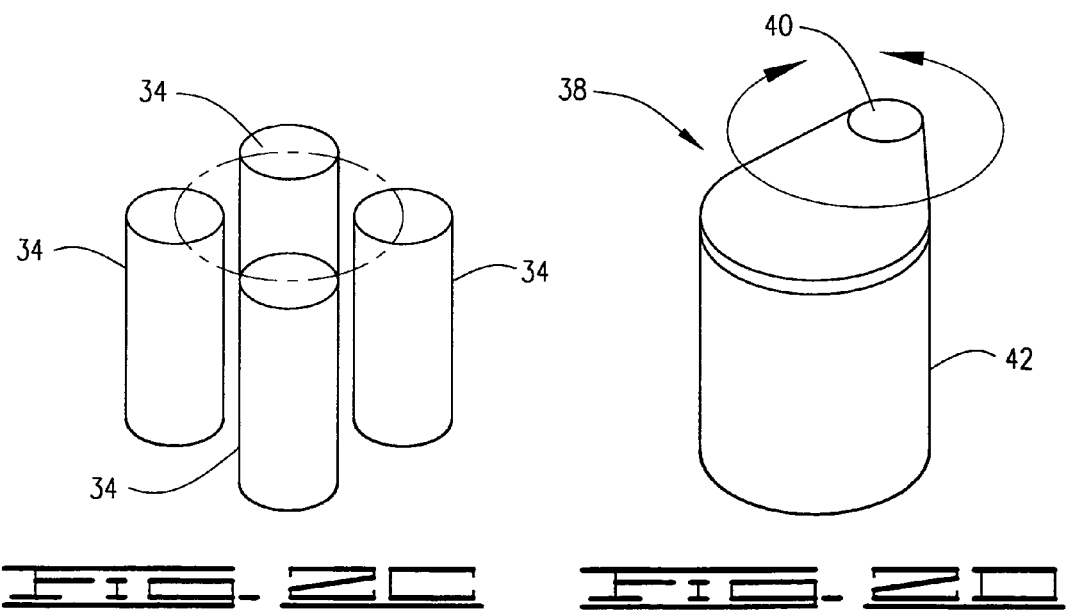

FIGS. 2B-2D show other preferred configurations for electromagnets, permanent magnets, and combinations of electromagnets and permanent magnets. For example, a preferred magnet configuration shown in FIG. 2C comprises electromagnets 34 clustered symmetrically around a center point and directed in parallel. The direction of the magnetic field is varied by varying or pulsing, preferably not in unison but rather alternately, the strength of the individual electromagnets. As above, alternate pulsing causes a variation in the direction of the resultant gradient at the membrane, causing the force acting upon magnetic particles to vary in direction so as to aid particles in moving through the membrane. Another preferred arrangement is shown in FIG. 2B wherein a number of electromagnets 34 are clustered around a central magnet. As previously described, the electromagnets 34 are preferably pulsed alternately in a repetitive manner while the electromagnetic field from the main magnet 36 may remain constant.

A device for changing the direction of the magnetic field repetitively and continuously using only a mechanical device is shown in FIG. 2D. The eccentric rotating permanent magnet 38 comprises a rotating magnetic cap 40 on top of the magnet base 42. The cap 40 has a high magnetic susceptibility but is not symmetrical about the main axis of the magnet. Rotating the cap 40 on the magnet 38 causes the direction of the magnetic field passing through the targeted region to vary continuously as the cap is rotated.

The arm 22 can be modified such that the configurations shown FIGS. 2A-2C include independent and repetitive mechanical motion of the magnets to, for example, repetitively change the angle of the magnetic field at any point in the field. The devices shown in FIGS. 2A-2D can actually be modified in a number of ways to vary, in a repetitive manner, the overall strength of the magnetic field gradient and/or the direction of the magnetic field gradient. It is anticipated that the effectiveness of varying the strength or direction of the field will depend on the specific application. For example, if the particles are being pulled from a flowing stream it may be more effective to vary the direction but to always have a field acting so that particles that have not entered the membrane are not swept past the targeted location. In other cases, the space available for the magnets may be limited in the vicinity of the targeted area, so a system with a single magnet may be more suitable for the application.

Modification of the magnetic field using a magnet in a C or H configuration may also be beneficial in some cases. One pole could be a single pole and the other a configuration similar to those shown in FIGS. 2A-2C. It may also be beneficial to have both poles similar to the configuration shown in FIGS. 2A-2C with the pulsing or variation of the magnets being synchronized between the two poles where "pole" refers to the arrangement of magnets or mechanical devices shown in FIGS. 2A-2C rather than the end of a single, simple magnet.

The positioning means 22 is preferably a mechanical arm adjustably attaching the magnet(s) and providing stability and controlled positioning with respect to the membrane. Such positioning means are well known to those skilled in the art and are used, for example, in angioplasty procedures for remote guidance of intravascular catheters.

A system of the present invention for moving magnetic nanoparticles through a membrane comprises a means for introducing magnetically responsive nanoparticles into a body and a magnetic field generating device as described above. Means for introducing the magnetically responsive nanoparticles include, but are not limited to, injection of the particles into a person via the circulatory system and magnetic guidance to the membrane.

A method of the present invention for moving magnetically responsive nanoparticles through a membrane within a body comprise the steps of introducing the magnetically responsive nanoparticles into the body as described above, and moving the nanoparticles through the membrane using a varying-gradient magnetic field as described above.

In order to further illustrate the devices, systems and methods of the present invention, the following examples are given.

EXAMPLE

It was speculated that magnetic particles show a slow response to a continuous magnetic field when pulled through a membrane due to simple misalignment with pores in the membrane. Particles could also become trapped on the wall of channels going through the membranes, or in fibrous membranes, the particles could become entangled in the fibers as they move through. Changing direction of particle movement could assist particles to realign, to move past matter that accumulates in front of the particles, or to move off the wall of the pores as the particles are being pulled through the membrane.

Also, the probability of the particles becoming attached to the wall of a pore is greater when the maximum magnetic gradient is at a significant angle to the axis of pore. Therefore, changing the angle of the magnetic gradient should result in moving the particles off the wall of pore. Similarly, shutting off the magnetic field should allow the particles to diffuse off the wall of the pore and thus become free to move through the tissue.

Figure 3:
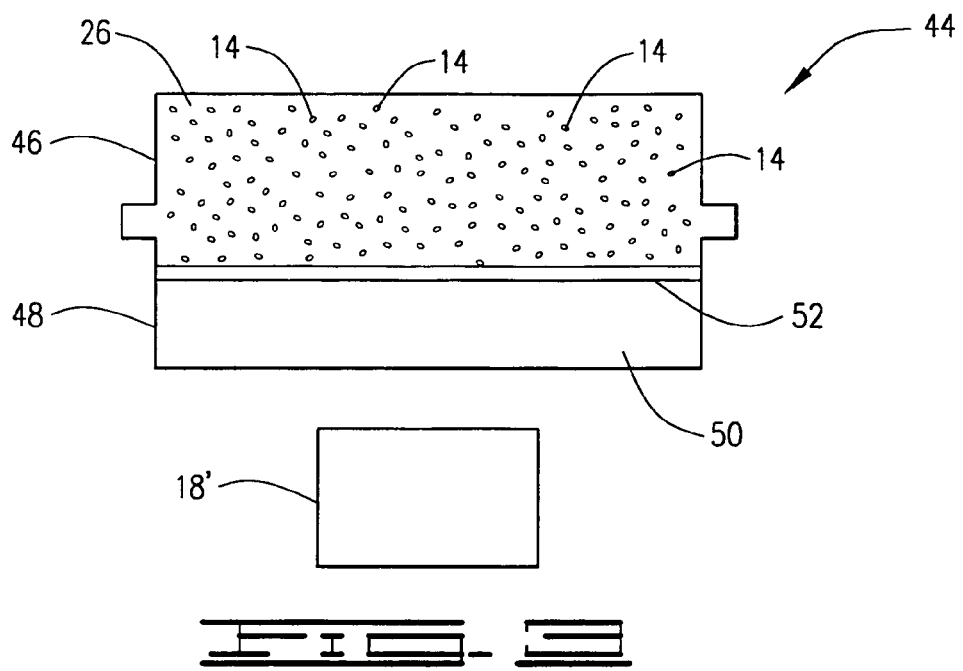
FIG. 3 is a diagrammatic illustration of the fixed-magnetic field experimental setup.

Laboratory tests using a fixed, constant strength magnet were performed to determine the base case feasibility of moving magnetic particles through membranes. A test apparatus was arranged as shown in FIG. 3. The objective of the test was to pull magnetic nanoparticles present in the first chamber 46 through the porous membrane 52 and into the second chamber 48. A stationary electromagnet 18' was used to pull magnetite nanoparticles from the carrier fluid 26 in chamber 46, across porous membrane 52, and into a clean fluid 50 in second chamber 48. Power to the electromagnet remained constant and the test ran for several hours. The results, evaluated visually, established that very few particles penetrated the membrane. It was concluded that the particles moved relatively slowly through the membrane.

A second test was then performed using a magnetic field that varied in strength. This test also utilized a test apparatus as shown in FIG. 3 except that the electromagnet 18' was operated in a pulsing or on/off mode. This was achieved by connecting the electromagnet to a controller having a switch and timer to turn the electromagnet on and off. The pulsation presumably allowed the particles to be released from membrane fibers or the walls of pores by diffusion.

Figure 4:
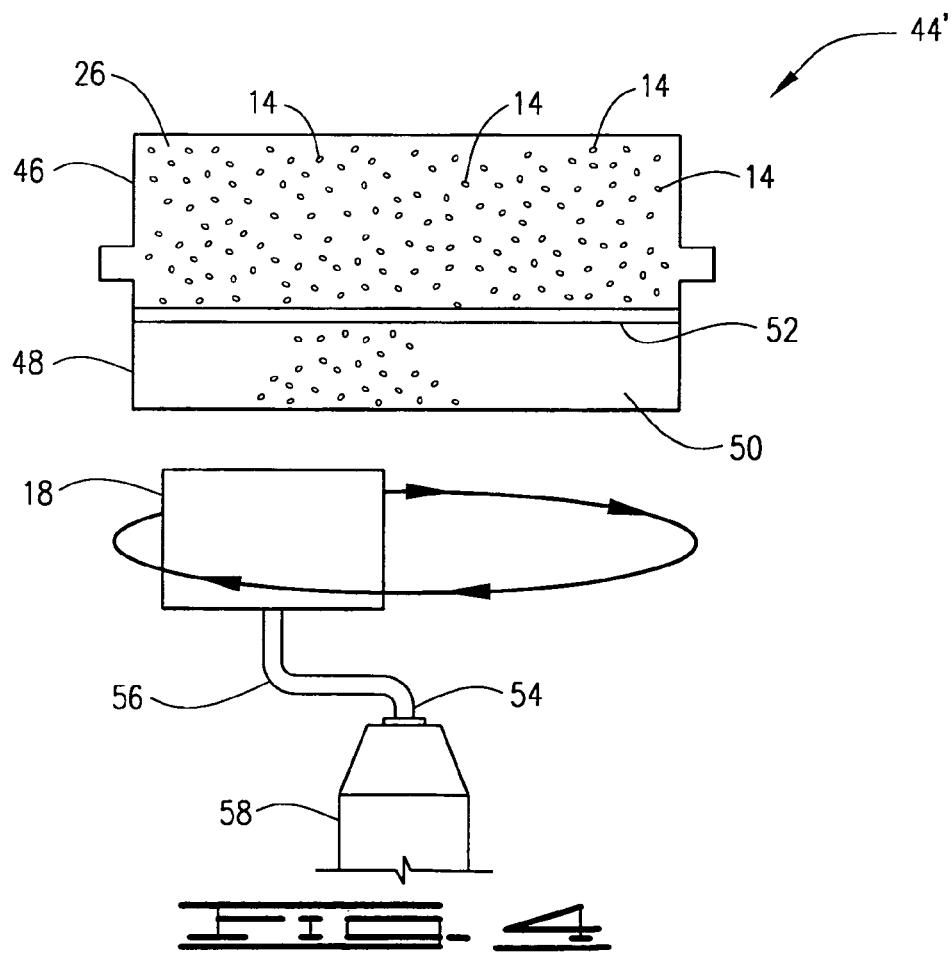
FIG. 4 is a diagrammatic illustration of a repetitively-varying magnetic field gradient experiment using a permanent magnet.

A third laboratory test was run in which the direction of the magnetic gradient was varied. The assembly is shown in FIG. 4. In this modification a permanent magnet 18 was attached to a steel rod 54 having two right angle bends 56. One end of the rod 54 was then attached to an electric motor 58 so that the magnet could be rotated at an estimated 30 to 60 rpm. Rotation of the magnet causes the components of magnetic gradient parallel to the face of the magnet to vary.

The second and third tests were also performed for several hours. The results were that significant quantities of particles appeared on the second chamber side of the membrane in both the second and third test. Also, significant quantities of particles were pulled to the bottom of the second laboratory chamber 48 in the third test. It was concluded that pulsation of the magnetic field and oscillating the magnetic field component perpendicular to the direction the particles are to be moved enhances particle movement through the laboratory porous membrane. Since varying the direction or strength of a magnetic field gradient aids the movement of particles through a laboratory porous membrane, it is likely the same effect will be operative in moving particles through living tissue or membrane.

Thus, the present invention is well adapted to attain the objects and advantages mentioned as well as those that are inherent therein. While numerous changes may be made by those skilled in the art, such changes are encompassed within the spirit of this invention as defined by the appended claims.

What is claimed is:

1. A method of using a magnetic field to move magnetically responsive nanoparticles through a membrane within a body comprising the following step:
    moving the nanoparticles through the membrane using a primary magnet to direct the nanoparticles in a primary direction, and at the same time, one or more secondary magnets directed at an acute angle relative to the primary direction, wherein the secondary magnets are controlled to repetitively vary the direction of the resultant magnetic field gradient in a pulsating manner.

2. The method of claim 1 wherein the magnetically responsive nanoparticles comprise ferromagnetic nanoparticles.

3. The method of claim 1 wherein the magnetically responsive nanoparticles comprise superparamagnetic nanoparticles.

4. The method of claim 1 wherein the membrane within the body comprises a tumor wall in a human body.

5. The method of claim 1 further comprising the step of embedding the nanoparticles in target cells.

6. The method of claim 5 wherein the nanoparticles carry a pharmaceutical.

7. The method of claim 6 wherein the pharmaceutical comprises a cancer-treating drug and the target cells are tumors.

8. The method of claim 5 wherein the nanoparticles impart magnetic properties to an organ comprising the target cells.

9. The method of claim 8 further comprising the step of applying magnetic stimuli to cause the organ to respond.

10. The method of claim 8 wherein the target cells are located in an ear of a human.

11. The method of claim 8 wherein the target cells are located in a valve of a human.

12. The method of claim 1 wherein the intensity of the magnetic field varies repetitively.

13. The method of claim 12 wherein the magnetic field intensity oscillates on and off.

14. The method of claim 1 wherein the magnetic field has an oscillating directional component.

15. The method of claim 1, further comprising the initial step of introducing the magnetically responsive nanoparticles into the body.

16. The method of claim 1, further comprising the step of positioning the primary and secondary magnets proximate the membrane.

17. The method of claim 1, wherein the primary magnet supplies at least about 50 percent of the total magnetic field.

18. The method of claim 1, wherein the secondary magnets are electromagnets, the electromagnets pulsed to provide the repetitively-varying magnetic field gradient at the membrane.

19. The method of claim 1, utilizing two secondary electromagnets alternately pulsed to provide the repetitively-varying magnetic field gradient at the membrane.

20. The method of claim 1, wherein the secondary magnets are moved or rotated about an axis in a manner to cause repetitive variation in the magnetic field gradient at the membrane.

* * * * *